United States Patent [19]

Bey et al.

[11] Patent Number: 5,066,828
[45] Date of Patent: Nov. 19, 1991

[54] DIFLUOROGLUTAMIC ACID CONJUGATES WITH FOLATES AND ANTI-FOLATES FOR THE TREATMENT OF NEOPLASTIC DISEASES

[75] Inventors: Philippe Bey; H. Michael Kolb, both of Cincinnati, Ohio

[73] Assignee: Merrell Dow Pharmaceuticals Inc., Cincinnati, Ohio

[21] Appl. No.: 508,874

[22] Filed: Apr. 12, 1990

[51] Int. Cl.$^5$ ............................................. C07C 229/24
[52] U.S. Cl. .................................... 560/171; 562/449; 562/573
[58] Field of Search ................. 560/171; 562/573, 449

[56] References Cited

U.S. PATENT DOCUMENTS 4,769,389  9/1988  Makovec et al. .................. 562/449

OTHER PUBLICATIONS

D. J. Cichowicz et al., *Bio. Chem. 26*, pp. 513-521, (1987).
J. J. McGuire et al., *J. Biol. Chem. 260*, pp. 6747-6754 (1985).
*Bio. Chem. Pharm. 34*, pp. 2995-2997 (1985).
N. J. Licato, et al., *J. Med. Chem.*, pp. 1022-1027 (1990).
Hogiman et al., Chem. Abst., vol. 87, #177664s, (1978).
McGuire et al., J. Biol. Chem., vol. 260, pp. 6747 (1985).

*Primary Examiner*—James H. Reamer
*Attorney, Agent, or Firm*—Stephen L. Nesbitt

[57] ABSTRACT

This invention relates to certain conjugates of folates and antifolates with difluoroglutamic acid which are useful in the treatment of patients suffering from certain neoplastic diseases including leukemia, melanomas, carcinomas, sarcomas and mixed neoplasias.

3 Claims, No Drawings

DIFLUOROGLUTAMIC ACID CONJUGATES WITH FOLATES AND ANTI-FOLATES FOR THE TREATMENT OF NEOPLASTIC DISEASES

FIELD OF THE INVENTION

This invention relates to novel difluoroglutamic acid conjugates with folates and anti-folates, to the use of these conjugates in the treatment of neoplastic diseases, and to intermediates used in the preparation of the conjugates.

BACKGROUND OF THE INVENTION

Folates and classical antifolates such as MTX[1] are converted intracellularly to poly($\gamma$-glutamyl) metabolites by the enzyme folylpolyglutamate synthetase.

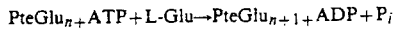

Since it is now known that folylpolyglutamates are essential to the proper functioning of folate metabolism, and antifolylpolyglutamates are implicated in the cytotoxic action of classical antifolates such as MTX, folylpolyglutamate synthetase has become an important enzyme for study in folate biochemistry and biochemical pharmacology. In this regard, the specificity of this enzyme for pteroyl and L-glutamate substrates has been extensively investigated. For pteroyl substrates, the structure of the heterocyclic component can vary considerably, but a terminal L-glutamate residue has been shown to be absolutely required for substrate activity in all reports to this time. Specificity for the incoming amino acid is strict, but not absolute. L-homocysteic acid and D,L-ervthro- or D,L-threo-4-fluoroglutamate can all serve as efficient alternate substrates, but in each case incorporation causes chain termination. Chain termination by the 4-fluoroglutamate diastereomers demonstrates the stringent specificity for L-glutamate at the $\gamma$-glutamyl acceptor site.

$F_2Glu$ is a potent, concentration-dependent inhibitor of poly($\gamma$-glutamylation) using [$^3$H]Glu and either methotrexate (4-$NH_2$-10-$CH_3$PteGlu) or tetrahydrofolate as substrates. Applicants have determined that $F_2Glu$ acts as an alternate substrate, but in contrast to the previously characterized alternate substrate 4-fluoroglutamate (McGuire and Coward, *J. Biol. Chem.* 260: 6747 (1985)), it did not terminate polyglutamate chain elongation. Instead, $F_2Glu$ promotes chain elongation. Thus, synthesis of products from [$^3$H]methotrexate containing 1 and 2 additional amino acid residues occurs at a substantially higher rate in the presence of $F_2Glu$ when compared to identical reactions in the presence of Glu; this is more pronounced for the product containing 2 additional residues. The increased rate of addition is not solely a function of ligating $F_2Glu$ to the internal Glu or to a previously incorporated $F_2Glu$, since ligation of Glu to 4-$NH_2$-10-$CH_3$PtGlu-$\gamma$-(3,3-difluoroglutamate) is also enhanced. These results are consistent with $F_2Glu$ enhancing the synthesis of poly($\gamma$-glutamate) metabolites at the level of either the incoming amino acid (glutamate analog) or the $\gamma$-glutamyl acceptor species. $F_2Glu$ is thus the first glutamate analog which enhances chain elongation catalyzed by folylpolyglutamate synthetase.

SUMMARY OF THE INVENTION

The compound 3,3-difluoroglutamate ($F_2Glu$) is used to prepare conjugates with certain folates and antifolates of formula 1

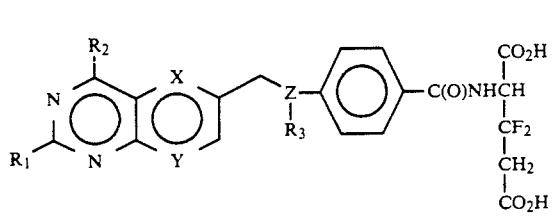

wherein $R_1$ is $-NH_2$, H, or $-CH_3$;
$R_2$ is $-NH_2$ or $-OH$;
$R_3$ is H, ($C_1$-$C_4$)alkyl, allyl, or propargyl, and
X, Y, and Z are each independently a nitrogen atom or a CH group;
and the pharmaceutically acceptable salts thereof. The structure 1 conjugates are useful in the treatment of tumors and psoriasis. Moreover the compound $F_2Glu$ and certain PABAF-$F_2Glu$ compounds are intermediates used in the preparation of the formula 1 compounds.

DETAILED DESCRIPTION OF THE INVENTION

The difluoro glutamate portion of the compounds of this invention possess an achiral center and thus the compounds of this invention exist as pairs of stereochemical isomers. While the enantiomer, corresponding to the natural configuration of L-glutamic acid, are preferred, applicants contemplate that both the individual isomers and mixtures of the individual isomers including the raceamic mixture are within the scope of this invention. Unless otherwise indicated the compounds of this application are mixtures of the two stereoisomers. Further, those compounds of formula 1 wherein Z is a CH group and wherein $R_3$ is other than a hydrogen have a second achiral site. The stereochemical configuration around this second achiral site is not critical and applicants again intend that the separate isomers and mixtures be included within the scope of this invention. A racemic mixture of isomers with regard to this second achiral site is preferred.

The compounds of formula 1 contain two carboxylic acid moieties and can form mono or di basic salts. Illustratively, these salts include those of alkali metals, as for example, sodium and potassium; alkaline earth metals, such as calcium and magnesium; light metals of Group IIIA including aluminum; and organic primary, secondary and tertiary amines, as for example, trialkylamines, including triethylamine, procaine, dibenzylamine, 1-ethenamine, N,N'-dibenzylethylenediamine, dihydroabietylamine, N-(lower)alkylpiperidine, and any other suitable amine. Sodium salts are preferred.

The compounds of formula 1 can also form pharmaceutically acid addition acceptable salts with any non-toxic, organic or inorganic acid. Illustrative inorganic acids which form suitable salts include hydrochloric, hydrobromic, sulphuric and phosphoric acid and acid metal salts such as sodium monohydrogen orthophosphate and potassium hydrogen sulfate. Illustrative organic acids which form suitable salts include the mono, di and tricarboxylic acids. Illustrative of such acids are, for example, acetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicylic, 2-phenoxybenzoic and sulfonic acids such as methane sulfonic acid and 2-hydroxyethane sulfonic acid. Hydrochloride salts are preferred.

The compounds of formula 1 can be prepared by protecting group removal from the product of the reaction of the formula 2 folate or antifolate derivative

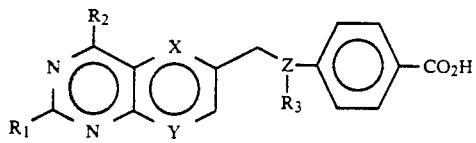

wherein $R_1$, $R_2$, $R_3$, X, Y, and Z are as defined above for the formula 1 compounds and a suitably protected derivative of $F_2$Glu such as the t-butyl ester derivative of formula 3, $F_2Glu(OtBu)_2$.

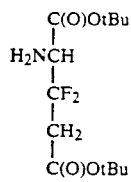

The coupling of the formula 2 compound and the protected $F_2$Glu derivative of formula 3 can be accomplished is any appropriate manner for preparing an amide from an amine and a carboxylic acid. Applicants have coupled the formula 2 and 3 compounds using diethyl phosphorocyanidate $((EtO)_2P(=O)CN)$. This reaction is performed by adding (slow dropwise addition) a solution of the appropriate formula 2 compound to a solution of $((EtO)_2P(=O)CN)$ and an acid scavenger such as pyridine, or preferably triethylamine. The resulting mixture is allowed to react at from about 0° C. to about 60° C., preferably at ambient temperature for from about 1 hour to about 10 hours, preferably from about 2 to about 5 hours, until the formula 2 compound is substantially reacted with the phosphorocyanidate. To this mixture is then added a solution of $F_2Glu(OtBu)_2$ and the resulting reaction is allowed to proceed for from about 24 hours to about 100 hours, generally for about 72 hours at from about 0° C. to about 60° C., preferably at ambient temperature. The crude product is isolated, for example, by solvent evaporation, washed with water and dried. The crude product is then treated with trifluoroacetic acid (neat) to remove the t-butyl ester protecting groups. The desired formula 1 compound is isolated and purified, for example, by column chromatography. Suitable solvents for the above described coupling reaction include any solvent in which the various reactants are soluble and which do not interfere with the reaction such as preferably dimethylformamide (DMF).

The compounds of formula 1 wherein Z is a nitrogen atom can be prepared by an alternative procedure in which a p-aminobenzoic acid (PABA) derivative of formula 4

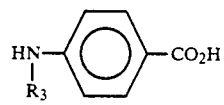

wherein $R_3$ is as defined above for the formula 1 compounds is reacted with the formula 3 compound, $F_2Glu(OtBu)_2$, to give the intermediate compound of formula 5

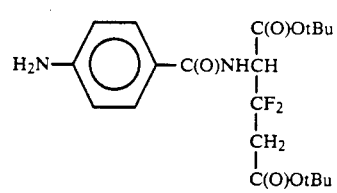

wherein $R_3$ is as defined above for the formula 1 compounds. This coupling can be accomplished in any suitable manner such as by the procedures described in McGuire, et al., *Cancer Research* 1989, 49, 4517–4525; Galican et al., *Proc. Natl. Acad. Sci.*, USA, 1985, 82, 2598–2602; Piper and Montgomery, *J. Org. Chem.*, 42(2) 208–211 (1977); Taylor, et al., *J. Med. Chem.* 28, 913–921 (1985); Taylor, et al., *J. Med. Chem.* 28, 1517–1522 (1985); Jones, et al., *J. Med Chem.* 32, 847–852 (1989).

The formula 5 intermediate is then condensed with the bromomethyl derivative of formula 6

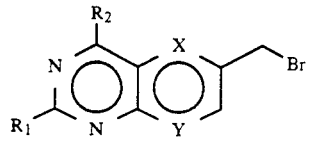

wherein $R_1$, $R_2$, X and Y are as defined for the formula 1 compounds above to produce the t-butoxy protected compounds which upon hydrolysis to remove the t-butoxy protecting groups such as with trifluoroacetic acid yield the desired compounds of formula 1. This reaction can be accomplished by allowing a mixture of the formulae 5 and 6 compounds and dimethylacetamide ($Me_2NAc$) to react for about 2 to about 12 hours, preferably for about 4 hours, at a temperature of from about 25° C. to about 80° C., preferably at about 50-55° C., and then leaving the reaction mixture stand at ambient temperature for from about 6 to about 24 hours, preferably for about 12 hours. The $Me_2NAc$ is then removed under reduced pressure and the crude material placed in an ice bath and treated with trifluoroacetic acid, allowing the mixture to warm to room temperature after addition is complete. After standing for from about 1 to about 6 hours, typically for about 4 hours, the TFA is removed under reduced pressure to give the crude desired product of formula 1. This product can be purified by, for example, chromatography (DEAE-cellulose with an $NH_4HCO_3$ gradient). This condensation reaction is more completely described in the references mentioned in the preceding paragraph.

The selection and utilization of particular blocking groups are well known to one of ordinary skill in the art. In general, blocking groups should be selected which adequately protect the amino or hydroxy groups in question during subsequent synthetic steps and which are readily removable under conditions which will not cause degradation of the desired product. Examples of suitable hydroxy protecting groups are $C_1$-$C_6$ alkyl, tetrahydropyranyl, methoxymethyl, methoxyethoxymethyl, t-butyl, benzoyl, and triphenylmethyl. The term $C_1$-$C_6$ alkyl refers to a saturated hydrocarbyl radical of one to six carbon atoms of straight, branched, or cyclic configuration. The benzoylated derivative can be formed by reacting the unblocked compound with benzoyl chloride in the presence of pyridine. Examples of suitable amino protecting groups are benzoyl, formyl, acetyl, trifluoroacetyl, phthalyl, tosyl, benzenesulfonyl, benzyloxycarbonyl, substitutedbenzyloxycarbonyl (e.g., p-chloro,p-bromo, p-nitro, p-methoxy, o-chloro, 2,4-dichloro, and 2,6-dichloro derivatives), t-butyloxycarbonyl (Boc), t-amyloxycarbonyl, isopropyloxycarbonyl, 2-(p-biphenyl)-isopropyloxycarbonyl, allyloxycarbonyl, cyclopentyloxycarbonyl, cyclohexyloxycarbonyl, adamantyloxycarbonyl, phenylthiocarbonyl, and triphenylmethyl. Preferred amino protected compounds include the benzoyl derivative, made by reacting the unblocked compound with benzoyl chloride, and the acetyl derivative, made by reacting the unblocked compound with acetic anhydride.

The present invention provides a method of treating a patient suffering from a neoplastic disease comprising administering to the patient a therapeutically effective antineoplastic amount of a compound of formula 1. By administering a therapeutically effective antineoplastic amount of a compound of formula 1 to a patient suffering from a neoplastic disease, an antineoplastic effect is provided. The term "patient" refers to a warm-blooded animal, such as primates, including humans, sheep, horses, cattle, pigs, dogs, cats, rats and mice.

The term "neoplastic disease" as used herein refers to an abnormal state or condition characterized by rapidly proliferating cell growth or neoplasm. Based upon standard laboratory experimental techniques and procedures well known and appreciated by those skilled in the art, as well as upon comparisons with compounds of known usefulness, the compounds of formula 1 are useful in the treatment of patients suffering from those neoplastic diseases which generally are or can be treated with folates and antifolates such as methotrexate, aminopterin, 5,10-dideazafolate and leucovorin. Such neoplastic diseases include: leukemias, including but not limited to acute lymphoblastic, chronic lymphocytic, acute myloblastic and chronic mylocytic; carcinomas, including but not limited to those of the cervix, esophagus, stomach, small intestines, colon and lungs; sarcomas, including but not limited to oesteroma, osteosarcoma, lipoma, liposarcoma, hemangioma and hemangiosarcoma; melanomas, including amelanotic and melanotic; and mixed types of neoplasias such as, for example, carcinosarcoma, lymphoid tissue type, folicullar reticulum, cell sarcoma and Hodgkins Disease. Of course, one skilled in the art will recognize that not every compound of formula 1 will be effective against each of the neoplastic disease states, and that selection of the most appropriate compound is within the ability of one of ordinary skill in the art and will depend on a variety of factors including assessment of results obtained in standard animal tumor models. In general the compounds of formula 1 are useful in the treatment of those neoplastic diseases currently treated with folates and antifolates. The compounds of this invention are expected to be more potent and more selective than are the non-conjugated folates and antifolates. The added potency of the compounds of this invention is believed to result from the tendency of the compounds to promote glutamyl chain enlogation and thereby cause accumulation of the toxic folate and antifolates within the cell.

The term "antineoplastic effect" and the term "treating a neoplastic disease" refers to an effect of controlling the growth or proliferation of the neoplasm or in prolonging the survivability of the patient beyond that expected in the absence of such treatment. The growth or proliferation of a neoplasm is controlled by slowing, interrupting, arresting or stopping its growth, proliferation or its metastases. The term "treating a neoplastic disease" therefore does not necessarily indicate a total elimination of the neoplastic disease. It is believed that prolonging the survivability of a patient, beyond being a significant advantageous effect in and of itself, also indicates that the growth of the neoplastic disease has been controlled.

In effecting treatment of a patient afflicted with a neoplastic disease described above, a compound of formula 1 can be administered in any form or mode which makes the compound bioavailable in therapeutically effective antineoplastic amounts, including oral and parenteral routes. For example, compounds of formula 1 can be administered orally, topically, subcutaneously, intramuscularly, intravenously, transdermally, intranasally, rectally, and the like. Oral administration is generally preferred. One skilled in the art can readily select the proper form and mode of administration depending upon the particular characteristics of the compound selected the disease state to be treated, the stage of the disease, and other relevant circumstances.

As used herein, the term "therapeutically effective antineoplastic amount" refers to an amount of the compound of formula 1 which is effective in providing an antineoplastic effect. A therapeutically effective antineoplastic amount can be readily determined by the attending diagnostician, as one skilled in the art, by the use of known techniques and by observing results obtained under analogous circumstances. In determining the therapeutically effective antineoplastic amount, a number of factors are considered by the attending diagnostician, including, but not limited to: the species of mammal; its size, age, and general health; the specific disease involved; the degree of or involvement or the severity of the disease; the response of the individual patient; the particular compound administered; the mode of administration; the bioavailability characteristics of the preparation administered; the dose regimen selected; the use of concomitant medication; and other relevant circumstances.

A therapeutically effective antineoplastic amount of a compound of formula 1 is expected to vary from about 0.1 milligram per kilogram of body weight per day (mg/kg/day) to about 500 mg/kg/day. Preferred amounts are expected to vary from about 1 to about 20 mg/kg/day. These ranges are particularly reflective of effective amounts upon oral administration but also are reflective of the operable ranges for parenteral administration. Preferably from 1 to 4 daily doses would be administered typically with from 5 mg to 100 mg of active compound per dose.

Methotrexate and other folate and antifolate agents have also been employed in the treastment of psoriasis, a disease characterized by an increased rate epidermal cell proliferation. The compounds of formula 1, by virtue of functioning by the same underlying mechanisms are expected to be valuable new agents in the treatment of psoriasis, the antineoplastic dosage is the same as the antipsoriasis dosage, except that when the formula 1 compounds are used in the treatment of psoriasis topical application is preferred.

The compounds can be administered alone or in the form of a pharmaceutical composition in combination with pharmaceutically acceptable carriers or excipients, the proportion and nature of which are determined by the solubility and chemical properties of the compound selected, the chosen route of administration, and standard pharmaceutical practice. The compounds of formula 1, while effective themselves, may be formulated and administered in the form of their pharmaceutically acceptable acid addition salts for purposes of stability, convenience of crystallization, increased solubility and the like.

The compounds of formula 1 can be provided in compositions comprising an assayable amount of a compound of formula 1 in admixture with one or more inert carriers. These compositions are useful, for example, as assay standards, as convenient means of making bulk shipments, or as pharmaceutical compositions. An assayable amount of a compound of formula 1 is an amount which is readily measurable by standard assay procedures and techniques as are well known and appreciated by those skilled in the art. Assayable amounts of a compound of formula 1 will generally vary from about 0.001% to about 75% of the composition by weight. Inert carriers can be any material which does not degrade or otherwise covalently react with a compound of formula 1. Examples of suitable inert carriers are water; aqueous buffers, such as those which are generally useful in High Performance Liquid Chromatography (HPLC) analysis; organic solvents, such as acetonitrile, ethyl acetate, hexane and the like; and pharmaceutically acceptable carriers or excipients. These compositions are prepared by mixing the compound of formula 1 with the inert carriers utilizing techniques and methods which are well known and appreciated in the art.

More particularly, compounds of formula 1 can be provided in pharmaceutical compositions comprising a therapeutically effective antineoplastic amount of a compound of formula 1 in admixture or otherwise in association with one or more pharmaceutically acceptable carriers or excipients.

The pharmaceutical compositions are prepared in a manner well known in the pharmaceutical art. The carrier or excipient may be a solid, semi-solid, or liquid material which can serve as a vehicle or medium for the active ingredient. Suitable carriers or excipients are well known in the art. The pharmaceutical composition may be adapted for oral or parenteral use and may be administered to the patient in the form of tablets, capsules, suppositories, solution, suspensions, or the like.

The compounds of formula 1 may be administered orally, for example, with an inert diluent or with an edible carrier. They may be enclosed in gelatin capsules or compressed into tablets. For the purpose of oral therapeutic administration, the compounds may be incorporated with excipients and used in the form of tablets, troches, capsules, elixirs, suspensions, syrups, wafers, chewing gums and the like. These preparations should contain at least 4% of the compound of the invention, the active ingredient, but may be varied depending upon the particular form and may conveniently be between 4% to about 70% of the weight of the unit. The amount of the compound present in compositions is such that a suitable dosage will be obtained. Preferred compositions and preparations according to the present invention are prepared so that an oral dosage unit form contains between 5.0-300 milligrams of a compound of the invention.

The tablets, pills, capsules, troches and the like may also contain one or more of the following adjuvants: binders such as microcrystalline cellulose, gum tragacanth or gelatin; excipients such as starch or lactose, disintegrating agents such as alginic acid, Primogel, corn starch and the like; lubricants such as magnesium stearate or Sterotex; glidants such as colloidal silicon dioxide; and sweetening agents such as sucrose or saccharin may be added or a flavoring agent such as peppermint, methyl salicylate or orange flavoring. When the dosage unit form is a capsule, it may contain, in addition to materials of the above type, a liquid carrier such as polyethylene glycol or a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the present compounds, sucrose as a sweetening agent and certain preservatives, dyes and colorings and flavors. Materials used in preparing these various compositions should be pharmaceutically pure and nontoxic in the amounts used.

For the purpose of parenteral therapeutic administration, the compounds of formula 1 may be incorporated into a solution or suspension. These preparations should contain at least 0.1% of a compound of formula 1, but may be varied to be between 0.1 and about 50% of the weight thereof. The amount of the compound present in such compositions is such that a suitable dosage will be obtained. Preferred compositions and preparations according to the present invention are prepared so that a parenteral dosage unit contains between 5.0 to 100 milligrams of the compound of the invention.

The solutions or suspensions may also include the one or more of the following adjuvants: sterile diluents such as water for injection, saline solution, fixed oils, polyethylene glycols, glycerine, propylene glycol or other synthetic solvents; antibacterial agents such as benzyl alcohol or methyl paraben; antioxidants such as ascorbic acid or sodium bisulfite; chelating agents such as ethylene diaminetetraacetic acid; buffers such as acetates, citrates or phosphates and agents for the adjustment of tonicity such as sodium chloride or dextrose. The parenteral preparation can be enclosed in ampules, disposable syringes or multiple dose vials made of glass or plastic.

As with any group of structurally related compounds which possesses a particular generic utility, certain groups and configurations are preferred for compounds of formula 1 in their end-use application.

Applicants prefer those compounds in which $R_1$ and $R_2$ are each a $-NH_2$ group, X, Y and Z are each a nitrogen atom, and $R_3$ is a methyl group. Applicants also prefer those compounds in which $R_1$ is a $-NH_2$ group, $R_2$ is an OH group, $R_3$ is a hydrogen, X and Z are each a -CH group and Y is a nitrogen atom.

EXAMPLE 1

N-[4-([(2,4-Diamino-6-pteridinyl)methyl]methylamino)-benzoyl]-4,4-D-Fluoroglutamic acid A mixture of N-CH$_3$PABA-F$_2$Glu(OBu)$_2$ (0.201 mmol) and 2,4-diaminopteridine-6-bromomethyl hydrobromide (75 mg, 0.223 mmol) in Me$_2$NAc (2.5 ml) is stirred at 50-55° C. for 4 hr and then left at ambient temperature overnight. Me$_2$NAc is then removed under reduced pressure. This crude material is placed in an ice bath, and 2 ml of trifluoroacetic acid is added with stirring. After 10 min, the reaction mixture is allowed to warm to ambient temperature and is stirred for 4 hr. The trifluoroacetic acid is removed under reduced pressure giving the crude product. The crude product is purified by chromatography on DEAE-cellulose with an NH$_4$HCO$_3$ gradient (15-600 mM). Lyophilization of the column effluent containing the desired product gives the desired pure product.

EXAMPLE 2

4-Amino-4-deoxy-10-methylpteroyl[D,L-erythro,threo -4,4-(difluoro)glutamic acid] (1, R$_1$,R$_2$=NH$_2$; X,Y,Z=N;R$_3$=CH$_3$)

In a 15 mL round bottom flask fitted with a drying tube is placed 2.5 mL DMF, 23 μL Et$_3$N (0.16 mmol) and 25 μL (0.16 mmol) diethyl phosphorocyanidate. The diaminopteroate (1,R$_1$,R$_2$=NH$_2$; X,Y,Z=N;R$_3$=CH$_3$)(0.16 mmol) is then added and the reaction solution is stirred at ambient temperature. After 3 h, an additional 5 μL (0.04 mmol) of diethyl phosphorocyanidate is added. F$_2$Glu (0.16 mmol) is dissolved in 1 mL DMF and added to the reaction flask and stirring continued for 72 h at ambient temperature. Solvent DMF is removed in vacuo, the residue is dissolved in 35 mL CHCl3 and washed with 1% NH$_4$OH (2×20 mL) to remove unreacted starting material. The organic layer is washed with 20 mL H$_2$O, then dried over Na$_2$SO$_4$ and evaporated in vacuo to provide crude blocked product. This coupled material is dissolved in neat TFA (3 mL) and progress of the de-esterification reaction is monitored by TLC. After 24 h, the solvent TFA is removed by rotary evaporation and the residue dried in vacuo.

The crude product is dissolved in 20 mL H$_2$O, the pH adjusted to 8 with dilute NH$_4$OH, and the sample volume brought to 160 mL in order to obtain sufficiently low conductance prior to loading on a DEAE-cellulose (Whatman DE-52) column (30×1 cm). The column is washed with 100 mL water and the desired formula 1 compound is eluted from the column with a linear gradient formed from 175 mL of 15 mM NH$_4$HCO$_3$ and 175 mL of 500 mM NH$_4$HCO$_3$.

EXAMPLE 3

β,β-Difluoroglutamic acid bis-L-butyl ester 3a 2,2-Difluoropent-4-enamide

To a stirred solution of 2,2-difluoropent-4-enoic acid (27.2 g, 0.2 mol) in hexane (200 mL) in a three-neck flask equipped with a reflux condenser and N$_2$ inlet is added DMF (20 drops, catalytic) and oxalyl chloride (20 mL, 0.23 mol). The mixture is stirred at room temperature for 2 h, when no further evolution of gas is seen. The solution is cooled in an ice/brine bath, the N$_2$ inlet is replaced by an empty CaCl$_2$ tube (to trap any solid material blown out of the flask), and a stream of NH$_3$ gas is passed into the flask. The gas flow is maintained for 30 min after the initial vigorous reaction has subsided. The mixture is then poured into H$_2$O (1 L) and Et$_2$O (0.5 L). The glassware is washed with H$_2$O and Et$_2$O, and the washings are added to this mixture. Celite is added and insoluble material is removed by filtration. The phases are separated. The Et$_2$O phase is washed once with brine, dried over Na$_2$SO$_4$, and concentrated. The aqueous phase is extracted twice with CH$_2$Cl$_2$. The combined extracts are washed once with brine, dried over Na$_2$SO$_4$, combined with the residue of the ethereal phase, and concentrated. The residue is distilled to give the title amide (20.6 g, 76%) bp 100-110° C./10 Torr, as a slightly yellow oil which solidifies on cooling, mp 33-35° C. $^1$H NMR (CDCl$_3$) δ 7.0-6.0 (2H, br.d), 5.75 (1 H, ddt, J=18, 9, 6 Hz), 5.3 (2 H, m), 2.87 (2 H, dt, J =6, 17 Hz). $^{19}$F NMR (δ C$_6$F$_6$=O) δ−56.0 (t, J =17 Hz).

Anal. Calcd for C$_5$H$_7$F$_2$NO: C, 44.45; H, 5.22; N, 10.37. Found: C, 42.03; H, 4.74; N, 9.33.

3b 2,2-Difluoropent-4-enonitrile

To a solution of the above amide (3a) (20.6 g, 0.152 mol) in dry pyridine (25 mL, 0.31 mol) under N$_2$ cooled in an ice/brine bath is added dropwise over 1½ h, trifluoroacetic anhydride (TFAA, 23.5 mL, 0.166 mol). The reaction mixture becomes solid, and is allowed to stand at room temperature for 4 h. The flask is then equipped for distillation under N$_2$ and heated in an oil bath (finally at 130° C.). The distillate is collected to give 17.7 g of colorless oil which fumes in air, bp 70-80° C./760 Torr. Analysis by NMR indicates that the composition of the distillate is nitrile:TFAA:pyridine 80:12:8. Hence the yield of nitrile is 0.116 mol (76%). $^1$H NMR (CDCl$_3$) 6.0-5.5 (1 H, m), 5.4 (2 H, m), 2.93 (2 H, dt, J=6, 15 Hz). $^{19}$F NMR (δ C$_6$F$_6$=O) δ−71.7 (t, J =15 Hz).

3c 4,4-Difluoroocta-1,6-dien-5-ylamine hydrochloride

Propenylmagnesium bromide is prepared by the addition of a solution of 1-propenyl bromide (27.22 g, 0.225 mol) in THF (225 mL) to magnesium turnings (5.47 g, 0.225 mmol) at such a rate as to maintain the mixture warm but not boiling. When the addition is complete the mixture is stirred for 20 min, then diluted with THF (300 mL) and cooled to −15° C. To this mixture is added a solution of the nitrile (0.116 mmol) prepared in example 3b in THF (80 mL) at a rate such that the temperature of the reaction mixture remains within the range −15<T<−10° C. The mixture is stirred for a further 1 h in this temperature range, and then cooled to −40° C. A cold (−40° C.) solution of NaBH$_4$ (6.4 g, 0.169 mol) in MeOH (650 mL) and water (30 mL) is added in one portion. The cooling bath is removed and the mixture is stirred for 2 h, then poured into 6 N HCl (800 mL). The organic solvents are removed by rotary eevaporation, and the aqueous solution is washed twice with CH$_2$Cl$_2$. The solution is then basified to pH 10 with NaOH pellets (ice-cooling is necessary), and saturated with NaCl. Celite is added and the precipitated Mg(OH)$_2$ is removed by filtration. The solid residue is washed with CH$_2$Cl$_2$. The filtrate is extracted with CH$_2$Cl$_2$ three times, and the combined extracts and residue washings are dried over Na$_2$SO$_4$, filtered, acidified with Et$_2$O/HCl, and evaporated to give the title amine salt as a pale yellow solid (3 g). This material is not purified at this stage.

3d N-(t-Butyloxycarbonyl)-4,4-difluoroocta-1,6-dien-5-ylamine

The above crude salt of example 3c (35 g) is dissolved in water (200 mL) and dioxan (200 mL). Solid KHC03 is added to give a mixture which is neutral to pH paper, to which is added further KHC03 (12 g, 0.12 mol) and di-t-butyldicarbonate (34 g, 0.156 mol). The mixture is stirred at room temperature overnight and then saturated with NaCl. The phases are separated. The aqueous phase is extracted with hexane (×3). The extracts are combined with the organic phase and washed with water (×3). The combined aqueous washings are extracted once with hexane. This extract is combined with the organic phases which are then washed with brine, dried over $Na_2SO_4$, and concentrated. The residue is purified by flash chromatography (eluant $CH_2Cl_2$/pentane 1/1) to give the title carbamate (19 g, 65%), $R_f$ 0.29, as an oil which soldifies on standing. $^1H$ NMR ($CDCl_3$) δ 6.0–5.5 (2 H, m); 5.5–4.5 (5 H, m); 2.67 (2 H, dt, J=7, 16 Hz); 1.73 (3 H, dd*, J=7,1 Hz); 1.47 (9 H, s). $^{19}F$ NMR (δ $C_6F_6$=0) δ−53.2 (m).

3e β,β-Difluoroglutamic acid hydrochloride

To an ice-cold solution of $KMnO_4$ (52.56 g, 0.33 mol) in $H_2O$ (1.2 L) is added a solution of the carbamate prepared in example 3d (10.95 g, 0.042 mol) in AcOH (160 mL). The mixture is stirred overnight at room temperature, during which time a brown solid precipitates. Solid sodium disulphite is added to decolorize the mixture, followed by conc. HCl to give a solution of pH 2. This solution is extracted with $Et_2O$ (3×500 mL), then saturated with NaCl and further extracted twice with $Et_2O$. The combined organic fractions are washed once with brine and concentrated. The residue is taken up in 1 N HCl (500 mL) and concentrated. The residue is once again taken up in 1 N HCl, the mixture is warmed, and activated charcoal is added. The mixture is stirred for 10min, filtered, and the filtrate is evaporated to dryness. Extraction of the residue with hot isopropanol gives the crude amino acid (2.22 g). Further extraction of the isopropanol insoluble material with EtOH does not give any useful material. $^{19}F$ NMR ($D_2O$: δ $CF_3CO_2H$=0) δ+23 (ddt, J=280, 5, 21 Hz),+27 (ddt, J=280, 22, 9 Hz); +28 (t); relative integrals 5:5:3.

3f β,β-Difluoroglutamic acid bis-t-butyl ester

The crude acid of example 3e (2.22 g) is suspended in t-butyl acetate (500 mL), and HClO4 (2.16 mL of 70% aqueous solution, 25 mmol) is added to the mixture. The mixture is stirred at room temperature for 48 h, and then extracted with $H_2O$ (2×200 mL). The combined extracts are washed with $CH_2Cl_2$ (2×100 mL) and then basified to pH 10 (4 N NaOH). The solution is extracted with $CH_2Cl_2$ (3×100 mL). The combined extracts are washed with brine, dried over $Na_2SO_4$, and concentrated to one third of their volume. This solution can be used for the next step without further treatment. A sample evaporated more completely shows $^1H$ NMR ($CDCl_3$) δ 4.10 (1 H, t, J =14 Hz), 3.10 (1 H, t, J =15 Hz), 3.00 (1 H, t, J=15 Hz), 1.5 (18 H, 2 s); $^{19}F$ NMR (δ $C_6F_6$=O) δ−58.7 (dt, J=14, 15 Hz).

EXAMPLE 4

β,β-Difluoroqlutamic acid hydrochloride

To a solution of the BOC-bis-ester of example 3(300 mg, 0.76 mmol) in dry $Et_2O$ (10 mL) is added saturated $Et_2O$/HCl (3 mL). The mixture is stirred at room temperature ($CaCl_2$ tube protection) for 6 days. The precipitated white solid is collected and washed with $Et_2O$. Analysis by TLC and NMR indicates that cleavage of the esters is not complete. The material is taken up in 1 N HCl (5 mL) and stirred at room temperature overnight. The reaction is still not complete. A few drops of conc. HCl are added, and the mixture is stirred for 3 days. The water is removed in vacuo and the residue is dried by azeotropic evaporation with $CCl_4$. Trituration with diisopropyl ether (×2) gives a slightly green powder, which is collected and dried over $P_2O_5$ to give the title amino acid (175 mg, 100%). $^1H$ NMR ($D_2O$). Signals obscured by solvent. $^{19}F$ NMR (δ $CF_3CO_2H$=O) δ+23 (ddt, J =280, 5, 21 Hz), +27 (ddt, J =280, 22, 9 Hz). MS (CI, $NH_3$) m/e 184 (MH+, 100%), 140 (75%), 120 (40%), 102 (40%). Rf (HOAc/H20/BuOH 1/1/3) 0.19.

Anal. Calcd. for $C_5H_7F_2NO_4$.HCl: C, 27.35: H, 3.67; N, 6.38. Found C, 28.13; H, 3.58; N, 6.52.

We claim:

1. A compound of the formula

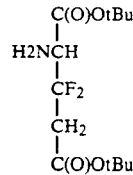

or a basic or an acid addition salt thereof.

2. A compound of the formula

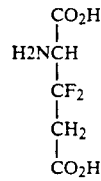

or a basic or an acid addition salt thereof.

3. A compound of the formula

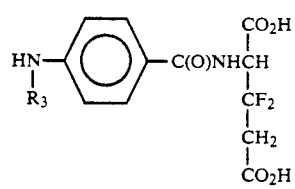

wherein $R_3$ is H, ($C_1$-$C_4$)alkyl, allyl, or propargyl or a basic or an acid addition salt thereof.

* * * * *

UNITED STATES PATENT AND TRADEMARK OFFICE
CERTIFICATE OF CORRECTION

PATENT NO.   : 5,066,828
DATED        : November 19, 1991
INVENTOR(S)  : Philippe Bey and H. Michael Kolb

It is certified that error appears in the above-identified patent and that said Letters Patent is hereby corrected as shown below:

At Column 2, line 25, the patent reads "PABAF-F$_2$Glu" and should read --PABA-F$_2$Glu--. At Column 3, line 35, the patent reads "is any" and should read --in any--. At Column 5, line 14, the patent reads "substitutedbenzyloxycarbonyl" and should read --substituted-benzyloxycarbonyl--. At Column 6, line 33, the patent reads "selected the" and should read --selected, the--. At Column 6, line 66, the patent reads "treastment" and should read --treatment--. At Column 9, line 32, the patent reads "CHCl3" and should read --CHCL$_3$--. At Column 10, line 51, the patent reads "eevaporation" and should read --evaporation--. At Column 10, lines 65 and 67, the patent reads "KHCO3" and should read --KHCO$_3$--. At Column 11, line 27, the patent reads "HCI" and should read --HCl--. At Column 11, line 30, the patent reads "10min," and should read --10 min,--. At column 11, line 40, the patent reads "HClO4" and should read --HClO$_4$--.

Signed and Sealed this

Twenty-fourth Day of August, 1993

Attest:

BRUCE LEHMAN

*Attesting Officer*     Commissioner of Patents and Trademarks